United States Patent
Katsumoto et al.

(10) Patent No.: US 9,463,267 B2
(45) Date of Patent: Oct. 11, 2016

(54) ARRAY OF ELEMENTS AND A HUMAN-COMPUTER INTERFACE DEVICE

(71) Applicants: National University of Singapore, Singapore (SG); Keio University Graduate School of Media Design, Yokohama (JP)

(72) Inventors: Yuichiro Katsumoto, Singapore (SG); Hideaki Nii, Tokyo (JP); Masahiko Inakage, Yokohama (JP)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 165 days.

(21) Appl. No.: 14/352,609

(22) PCT Filed: Oct. 19, 2012

(86) PCT No.: PCT/SG2012/000395
§ 371 (c)(1),
(2) Date: Apr. 17, 2014

(87) PCT Pub. No.: WO2013/058716
PCT Pub. Date: Apr. 25, 2013

(65) Prior Publication Data
US 2014/0268529 A1    Sep. 18, 2014

Related U.S. Application Data

(60) Provisional application No. 61/549,968, filed on Oct. 21, 2011.

(51) Int. Cl.
| | | |
|---|---|---|
| G06F 3/01 | (2006.01) |
| A61M 1/28 | (2006.01) |
| G06F 3/033 | (2013.01) |
| G06F 3/02 | (2006.01) |
| A61M 1/16 | (2006.01) |
| B01D 61/30 | (2006.01) |
| G01N 33/00 | (2006.01) |
| G01N 1/14 | (2006.01) |

(52) U.S. Cl.
CPC ............. *A61M 1/28* (2013.01); *A61M 1/1609* (2014.02); *A61M 1/1696* (2013.01); *B01D 61/30* (2013.01); *G01N 33/0021* (2013.01); *G06F 3/0202* (2013.01); *G06F 3/033* (2013.01); *G01N 33/0054* (2013.01); *G01N 2001/1454* (2013.01)

(58) Field of Classification Search
CPC ...... G06F 3/017; G06F 3/0202; G06F 3/033; A61M 1/1609; A61M 1/1696; A61M 1/28; B01D 61/30; G01N 33/0021; G01N 33/0054; G01N 2001/1454
USPC ............ 361/679.01, 679.02, 679.03, 679.04, 361/679.4
See application file for complete search history.

(56) References Cited

U.S. PATENT DOCUMENTS

| 5,491,651 A * | 2/1996 | Janik ....................... G06F 1/163 361/679.03 |
| 8,766,926 B2 * | 7/2014 | Wirtanen .............. G06F 3/0346 178/18.01 |
| 2011/0089903 A1 * | 4/2011 | Heikkinen .......... H01M 2/1022 320/126 |

*Primary Examiner* — Anthony Haughton
*Assistant Examiner* — Ingrid Wright
(74) *Attorney, Agent, or Firm* — Moser Taboada

(57) ABSTRACT

A human-computer interface device comprising an array of elements wherein each element is pivotally coupled to an adjacent first element by a first pivotal coupling and to an adjacent second element by a second pivotal coupling, the first pivotal coupling being operable to pivot about an axis which is substantially orthogonal to an axis about which the second pivotal coupling is operable to pivot.

18 Claims, 4 Drawing Sheets

ARRAY OF ELEMENTS AND A HUMAN-COMPUTER INTERFACE DEVICE

FIELD OF INVENTION

Various embodiments of the invention relate to an array of elements and to a human-computer interface device. The array may comprise at least four elements to form a grid, wherein each element of the grid may be pivotally coupled to each adjacent element in the grid.

BACKGROUND

Known input devices, such as keyboards, computer mice, gaming pads, and electronic musical instruments, facilitate human-computer interfacing. These input devices are typically capable of controlling the operation of a computer, wherein a user can control the computer by pushing, gripping, and/or moving the input devices.

These known input devices usually comprise a structure having fixed physical properties, such as, shape and/or size. Accordingly, the level of human-computer interaction provided by these known input devices is relatively limited.

A need therefore exists to provide a human-computer interface device and a structure thereof which seeks to address at least one of the abovementioned problems.

SUMMARY

Various embodiments provide an array of elements, wherein each element is pivotally coupled to an adjacent first element by a first pivotal coupling and to an adjacent second element by a second pivotal coupling, the first pivotal coupling being operable to pivot about an axis which is substantially orthogonal to an axis about which the second pivotal coupling is operable to pivot.

In an embodiment, at least four elements may be arranged to form a grid, each element of the grid may be pivotally coupled to each adjacent element in the grid.

In an embodiment, the grid may have a square shape or an elongate shape.

In an embodiment, each first pivotal coupling may be operable to pivot about the same axis to prevent each second pivotal coupling from pivoting.

In an embodiment, adjacent elements in the array of elements may be arranged side-by-side.

In an embodiment, the first pivotal coupling may be disposed substantially orthogonal to the second pivotal coupling.

In an embodiment, at least one pivotal coupling may be capable of only one degree of freedom.

In an embodiment, at least one pivotal coupling may comprise at least one hinge.

In an embodiment, at least one element in the array may comprise a substantially planar square shape having pivotal couplings positioned at a side portion thereof.

In an embodiment, at least one element in the array has at least one beveled side portion.

Various embodiments provide a human-computer interface device, comprising the array of elements as described herein.

In an embodiment, the human-computer interface device may comprise a controller configured in use to provide an output signal.

In an embodiment, the human-computer interface device may comprise at least one sensor in communication with the controller, the at least one sensor being operable to detect the relative displacement between at least two elements of the array and provide a corresponding signal to the controller, wherein the controller is operable to provide the output signal in dependence on the corresponding signal.

In an embodiment, the human-computer interface device may further comprise at least one button disposed on an element of the array, the at least one button being in communication with the controller, wherein the controller is operable to provide the output signal in dependence on activation of the at least one button.

In an embodiment, the human-computer interface device may further comprise at least one accelerometer for detecting motion of the human-computer interface device, the at least one accelerometer being in communication with the controller, wherein the controller is operable to provide the output signal in dependence on a signal received from the at least one accelerometer.

In an embodiment, the human-computer interface device may further comprise an output device in communication with the controller, the output device being configured to receive the output signal and provide an output in dependence thereon.

In an embodiment, the output may comprise a sound and/or tactile feedback.

In an embodiment, the human-computer interface device may comprise one or more actuators configured to displace one or more elements of the array.

In an embodiment, the human-computer interface device may further comprise a host computer interface device for enabling data transfer between the human-computer interface device and the host computer.

BRIEF DESCRIPTION OF THE DRAWINGS

Example embodiments of the invention will be better understood and readily apparent to one of ordinary skill in the art from the following written description, by way of example only, and in conjunction with the drawings, wherein like reference signs relate to like components, in which.

DETAILED DESCRIPTION

Example embodiments of the invention relate to an array of elements. Each element in the array may be pivotally coupled to an adjacent first element by a first pivotal coupling and to an adjacent second element by a second pivotal coupling. The first pivotal coupling may be operable to pivot about an axis which is substantially orthogonal (i.e.

perpendicular) to an axis about which the second pivotal coupling is operable to pivot.

The array of elements may be suitable for use in many applications, including, but not limited to, human-computer interfacing and physical rehabilitation.

Figure 1:
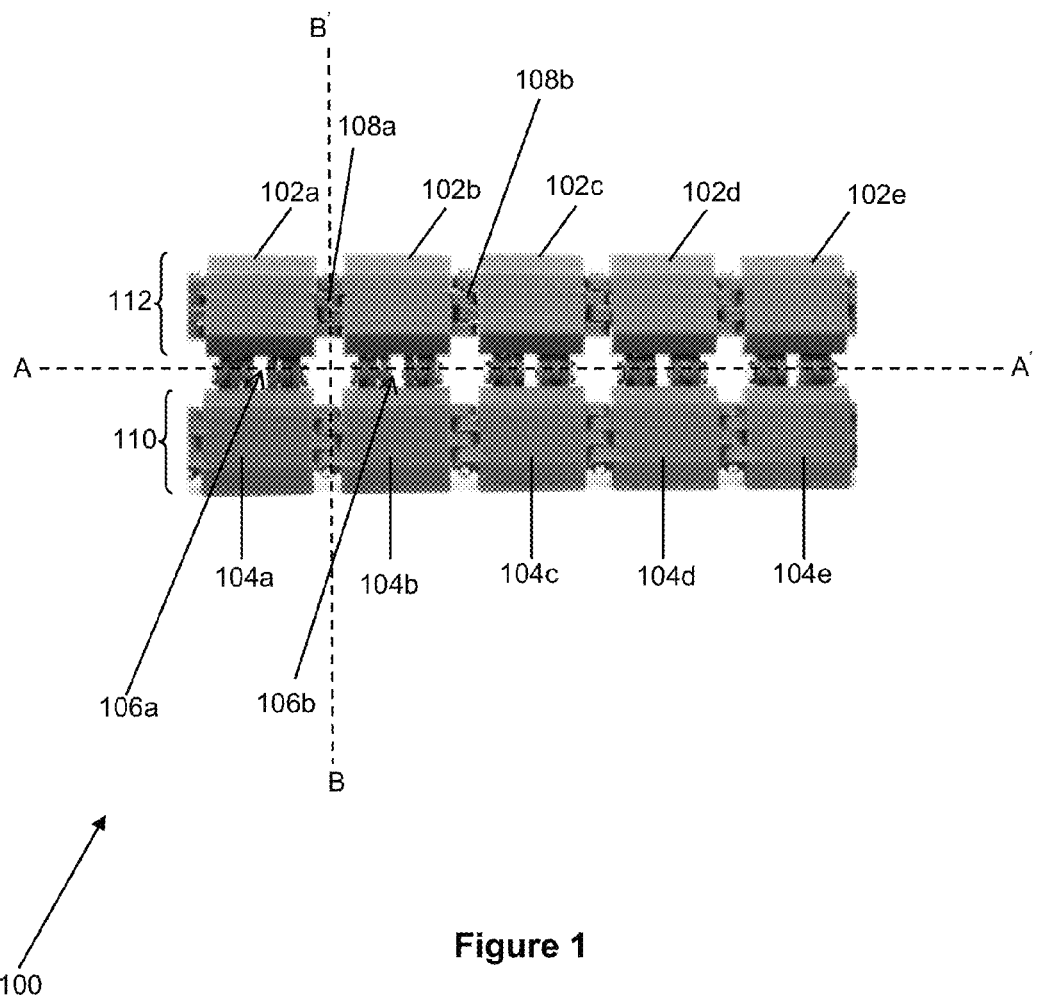
FIG. 1 is a plan view of an array of elements, according to an embodiment of the invention.

FIG. 1 is a plan view of an array 100 of elements 102a-e and 104a-e, according to an example embodiment of the invention. The elements 102a-e and 104a-e are arranged in two substantially parallel rows 112 and 110 to form an elongate shaped array 100. It will be appreciated by a person skilled in the art that, in another embodiment, the array may have a different number of elements, and/or the elements may be arranged in a different configuration to form a different shape. For example, the array may be square shaped rather than elongate shaped.

Elements in the array may comprise at least two pivotal couplings. In an embodiment, a pivotal coupling may comprise one or more hinges. However, in another embodiment, other types of pivotal coupling may be used, such as pin joints and ball-and-socket joints. In an embodiment, a pivotal coupling is capable of only one degree of freedom.

In an embodiment, at least a portion of a pivotal coupling may be formed integrally with an adjoining element. In an embodiment, a pivotal coupling may be formed integrally with its adjoining elements. However, in an embodiment, the pivotal coupling may be formed independently from its adjoining elements, but connected thereto by suitable fasters.

Referring to element 102b for illustrative purposes, each element in the array 100 may comprise two sets of hinges, for example, 106b and 108b. The first set of hinges 106b may be disposed substantially orthogonal to the second set of hinges 108a/108b. In other words, the first set 106b may be disposed substantially parallel to a longitudinal axis A-A' of the array 100; and the second set 108a/108b may be disposed substantially orthogonal to the longitudinal axis A-A' of the array 100, i.e. along axis B-B'.

The array 100 of elements may comprise a plurality of hinges disposed substantially parallel to the longitudinal axis A-A' of the array 100, for example, 106a and 106b (hereinafter referred to as "horizontal hinges"); and a plurality of hinges disposed substantially orthogonal to the longitudinal axis A-A' of the array 100 (i.e. along axis B-B'), for example, 108a and 108b (hereinafter referred to as "vertical hinges"). The horizontal and vertical hinges may act as pivotal couplings between respective adjacent elements. In the following description, the term "adjacent element(s)" may refer to immediate adjacent element(s) that are directly pivotally coupled together. For example, elements 102a and 104b are adjacent elements to element 102b; however, elements 104a and 102d are not adjacent elements to element 102b. In an example embodiment, adjacent elements are arranged side-by-side.

Referring again to element 102b for illustration, the element 102b may be pivotally coupled to adjacent elements 102a and 102c via vertical hinges 108a and 108b respectively; and coupled to adjacent element 104b via horizontal hinges 106b. Although two horizontal hinges 106b are shown in FIG. 1, it will be appreciated by a person skilled in the art that each element may have any suitable number of vertical and/or horizontal hinges depending on the particular application. For example, more hinges may be used when the array is expected to experience larger forces acting on it.

When the elements 102a-e of row 112 are co-planar with the elements 104a-e of row 110, the vertical hinges may allow adjacent elements that are pivotally coupled together by the vertical hinges to be pivoted relative to each other. For example, element 102a and element 102b may be pivoted relative to each other; and, element 104d and element 104e may be pivoted relative to each other. In this sense, the array 100 may act as a flexible member that is capable of bending about the vertical hinges in the array 100.

Figure 2A:
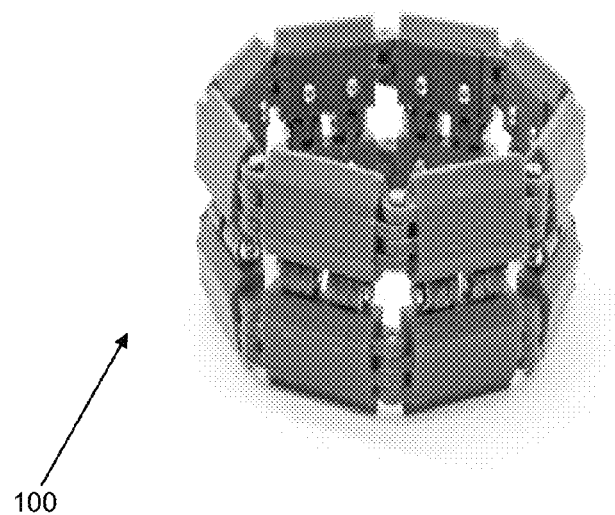
FIG. 2a is a perspective view of an array of elements, according to an embodiment of the invention, which is configured into a ring shape.
Figure 2B:
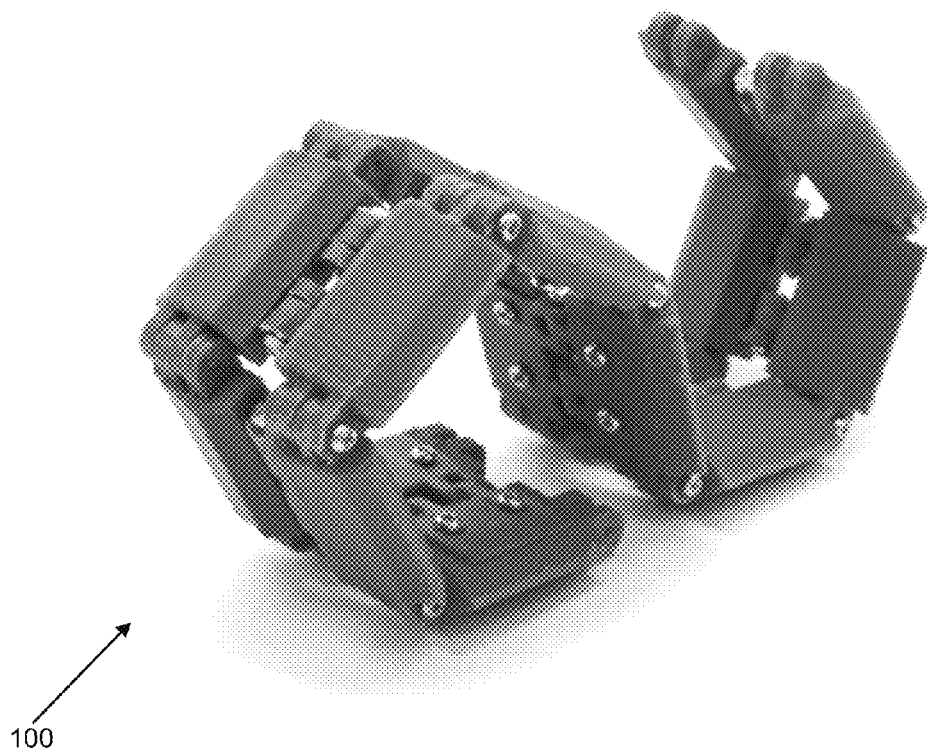
FIG. 2b is a perspective view of an array of elements, according to an embodiment of the invention, which is configured into a curved shape.

FIG. 2a is a perspective view of the array 100 which has been configured into a ring shape, i.e. one end of the array 100 has been connected to the other end to form a continuous loop. In an embodiment, both terminal end portions of the elongate array 100 may be fitted with a connector so that the two terminal ends can be connected together to form a continuous ring shape, as shown in FIG. 2a. FIG. 2b is a perspective view of the array 100 which is configured into a curved shape or, more specifically, a horizontal "S" shape.

Figure 3:
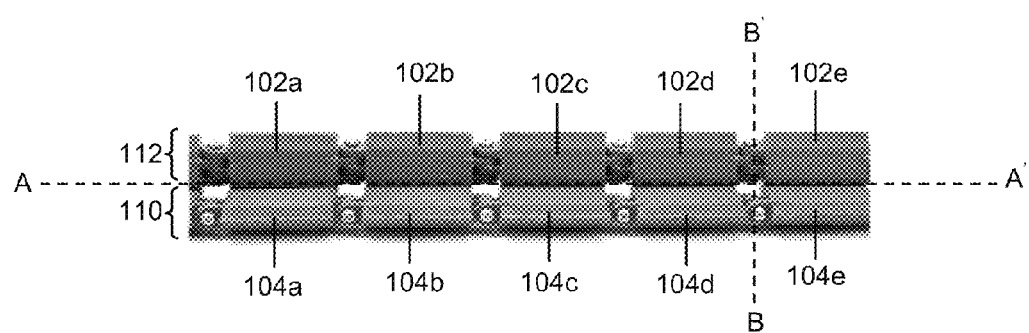
FIG. 3 is a perspective view of an array of elements, according to an embodiment of the invention, which is folded along a longitudinal axis of the array of elements A-A'.

FIG. 3 is a perspective view of the array 100 that is folded along the longitudinal axis of the array A-A'. In this instance, the horizontal hinges may pivot about the same axis, i.e. axis A-A'. The elements 102a-e of row 112 are displaced towards (i.e. folded towards) the elements 104a-e of row 110 in order to give the array a "V" shape cross-section. This advantageously prevents the vertical hinges from pivoting.

In other words, the horizontal hinges 106a-e (not clearly visible in FIG. 3) allow adjacent elements that are pivotally coupled together by the horizontal hinges to be pivoted relative to (i.e. folded towards) each other. For example, element 102a and element 104a can be pivoted relative to each other; element 102d and element 104d can be pivoted relative to each other, and so on. However, in this arrangement, adjacent elements that are pivotally coupled together by the vertical hinges may not be pivoted relative to each other. For example, element 102a and element 102b may not be pivoted relative to each other; element 104d and element 104e may not be pivoted relative to each other, and so on.

This arrangement may prevent the elements 102a-e and 104a-e in the array 100 from pivoting about a direction which is orthogonal to the longitudinal axis A-A' (i.e. along axis B-B') of the array 100. In this sense, the array 100 acts as a rigid elongate member that is not capable of bending about the vertical hinges 108a-e in the array 100.

In an example embodiment, at least four elements are arranged to form a grid. For example, with reference to FIG. 1, elements 102a, 102b, 104a and 104b are arranged to form a grid. In this embodiment, the term 'grid' is used to indicate that the elements are arranged to form aligned rows and aligned columns, such as, for example, those of a spreadsheet or graph paper. This grid arrangement allows the array of elements to alternate between the above-described flexible configuration and the above-described rigid configuration. The grid of at least four elements can take on a square or elongate shape. For example, the array of elements 100 shown in FIG. 1 comprises a grid having an elongate shape.

The array 100 may be able to alternate between a flexible configuration and a rigid configuration depending on the relative arrangement of the members. When the elements 102a-e of row 112 are co-planar with the elements 104a-e of row 110, the array 100 may act as a flexible elongate member. When the horizontal hinges pivot about the same axis, such as when the elements 102a-e of row 112 are displaced towards the elements 104a-e of row 110, the vertical hinges are prevented from pivoting. In this configuration, the array 100 may act as a rigid elongate member. This is possible because the pivotal couplings (which may provide one degree of freedom) may be disposed in an orthogonal manner (e.g. vertical and horizontal hinges). This orthogonal placement of the hinges may allow the vertical and horizontal hinges in the array to co-operate with each other to allow or prevent pivoting depending on the relative displacements of the elements in the array.

In an example embodiment, at least one element in the array is substantially square or elongate. Furthermore, each square or elongate element comprises one or more pivotal couplings such as hinges positioned at a side portion. One or more side portions may be beveled as shown in FIG. 1.

In an example embodiment, the elements are made of one or more hard, non-resilient material(s), such as, plastic (e.g. acrylonitrile butadiene styrene (ABS)) and/or metal. The pivotal couplings may be made of the same material, for example, if they are formed integrally with the elements. The pivotal couplings may be made of a different material, for example, if they are formed independently of the elements.

In an embodiment, each individual element may have a rectangular shape and have a length of about 30 mm, a width of about 20 mm, and a thickness of about 8 mm. In an embodiment, the term "about" may be taken as meaning ±5 mm.

The array described above may be used in many applications. The following description provides examples of the array being used for human-computer interfacing.

Figure 4:
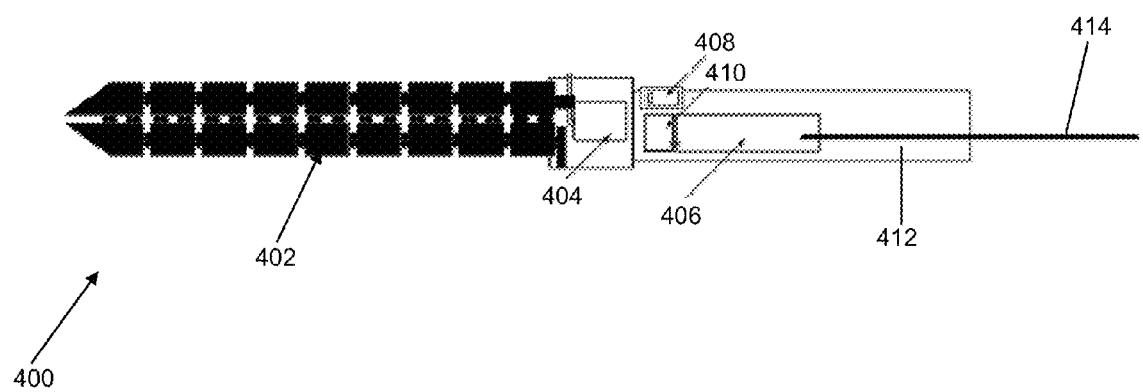
FIG. 4 is a schematic of a human-computer interface device, comprising an array of elements according to an embodiment of the invention.

FIG. 4 is a schematic of a human-computer interface device 400, comprising an array 402 of elements according to an embodiment of the present invention. The human-computer interface device 400 may further comprise: a microcontroller 406 (e.g. Arduino Pro Mini), a three-axis accelerometer 410, a servo motor 404, and a switch 408. Suitable software, such as Max/MSP, may be used to program the human-computer interface device 400 for different applications. A communication port (e.g. USB port) may be provided, for example, on the handle 412 of the device 400. The communication port may be used to connect a computer (not shown) with suitable software to the human-computer interface device 400 via a cable 414, for example, in order to facilitate data exchange between the device 400 and the computer. In an embodiment, the device 400 may be connected to the computer in order to program the microcontroller 406. In an embodiment, the cable may additionally or alternatively provide power to the device 400. In an embodiment, the human-computer interface device 400 may additionally or alternatively connect to the computer wirelessly, for example, using a transceiver (e.g. a WIFI transceiver) which may be positioned in the handle 412. In an embodiment, the communication port and/or the transceiver may be a host computer interface device.

The microcontroller 406, the three-axis accelerometer 410, the servo motor 404, and the switch 408 may be disposed within the handle 412 of the human-computer interface device 400.

In this example, the human-computer interface device 400 resembles a weapon. In a first state of operation, a user may use the device 400 as a whip. This arrangement may be possible when the elements 102a-e of row 112 are co-planar with the elements 104a-e of row 110 (as described above with respect to FIGS. 2a and 2b). In this arrangement, adjacent elements that are pivotally coupled together by vertical hinges may be pivoted relative to each other.

A second state of operation may be initiated by activating the switch 408. In the second state of operation the servo motor 404 may displace elements 102a-e of row 112 towards elements 104a-e of row 110 (as described above with respect to FIG. 3). In this instance, the horizontal hinges may pivot about the same axis and the vertical hinges may be prevented from pivoting. Adjacent elements that are pivotally coupled together by vertical hinges may not be able to be pivoted relative to each other, causing the array 402 to resemble a rigid elongate member, such as, a sword.

The three-axis accelerometer 410 may be configured to detect the user's motion. The human-computer interface device 400 may be configured to provide feedback (e.g. sound effects or tactile feedback) to a user based on variables, such as, the user's motion.

Figure 5:
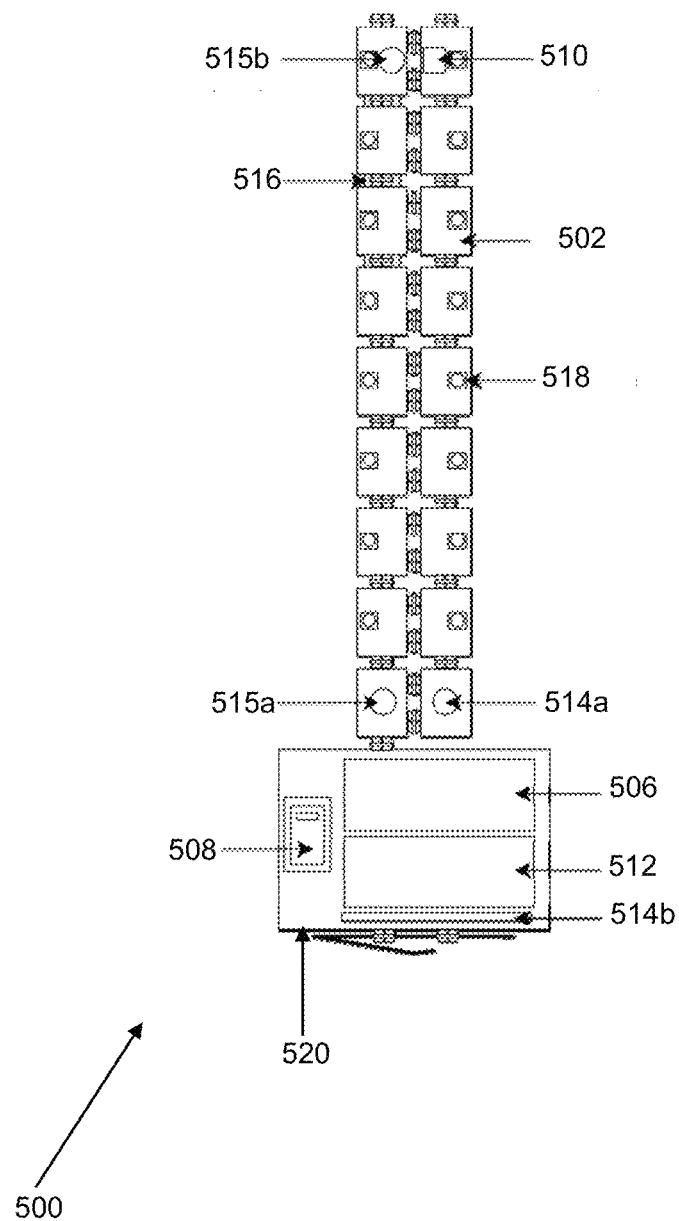
FIG. 5 is a schematic of a human-computer interface device, comprising an array of elements according to an embodiment of the invention.

FIG. 5 is a schematic of a human-computer interface device 500, comprising an array 502 of elements according to an embodiment of the present invention. The human-computer interface device 500 may further comprise a microcontroller 506 (such as xtel/MOXA, Xbee), a three-axis accelerometer 510, and a switch 508. Suitable software such as Max/MSP may be used to program the human-computer interface device 500 for different applications. A power source 512 (e.g. a LiPo battery with rating of 3.7V/ 1000 mAh) may be provided to power electronic components of the device 500. The power source 512, microcontroller 506 and switch 508 may be disposed within a base housing 520. The array 502 may be coupled to the base housing 520, for example, at an end portion when the array 502 is elongate.

One or more sensors may be placed on the array 502 to detect the relative displacements and/or positions of the elements in the array 502. In this example, one or more bend sensors (e.g. 516) may be coupled to one or more hinges to detect bending of the array 502. One or more three-axis accelerometers (e.g. 510) may be placed at suitable locations to detect motion of the array 502. Also, one or more reed switches 514a/b may be placed on the human-computer interface device 500 to detect bending of the array 502.

In use, the human-computer interface device 500 may be configured to resemble a flute or a recorder when the array 502 is flat, i.e. the elements are substantially co-planar. FIG. 5 illustrates this arrangement. The reed switch 514a, in co-operation with a magnet 515a, may be used to detect this arrangement. One or more buttons 518 (e.g. tact switches) may be placed on one or more elements of the array 502. Different buttons 518 may correspond to different musical notes. The human-computer interface device 500 may be configured to produce flute-like or recorder-like musical notes when the different buttons 518 are pressed.

The human-computer interface device 500 may also be configured to resemble a drum stick when the array 502 is folded along the longitudinal direction A-A' of the array 502 (as described above). In this configuration, the array may become an elongate rigid member. The reed switch 514a, in co-operation with a magnet 515a, may be used to detect this arrangement. The human-computer interface device 500 may be configured to produce drumbeats when the user shakes the human-computer interface device 500. The shaking of the human-computer interface device 500 may be detected, for example, by the three-axis accelerometer 510.

The human-computer interface device 500 may also be configured to resemble a saxophone when the array 502 is bent at a point distal the base housing 520 into a "j-shape". The bending of the array 502 may be detected, for example, by the one or more bend sensors (e.g. 516). Similarly, one or more buttons 518 (e.g. tact switches) may be placed on one or more elements on the array 502. Different buttons 518 may correspond to different musical notes. The human-computer interface device 500 may be configured to produce saxophone-like musical notes when the different buttons 518 are pressed.

The human-computer interface device 500 may further be configured into a ring shape when the array 502 is connected end-to-end to form a continuous loop. In other words, a portion of the array 502 distal the base housing may be connected to the base housing 520, for example, using cooperating connectors positioned on the distal end and on the housing. The reed switch 514*b*, in co-operation with a magnet 515*b*, may be used to detect this arrangement. The human-computer interface device 500 may be configured to produce bell chimes when the user presses one or more buttons 518 and/or shakes the human-computer interface device 500. Alternatively, the human-computer interface device 500 may be configured to produce harp-like sounds when the user rolls the ring-shaped human-computer interface device 500. The shaking or rolling of the human-computer interface device 500 may be detected, for example, by the three-axis accelerometer 510.

In the examples above, the shape of the human-computer interface device 500 (or more specifically, the shape of the array 502) may be varied to resemble different musical instruments. The human-computer interface device 500 may be configured to produce different sounds depending on its shape and/or movement (e.g. shaking, rolling, etc).

It will be appreciated by a person skilled in the art that the examples above are considered in all respects to be illustrative and not restrictive. The human-computer interface device 500 can be configured into different shapes to resemble other musical instruments that have not been disclosed herein, and to produce appropriate sounds when a predetermined action is performed (e.g. pressing a button, shaking, rolling, etc).

It is to be understood, that in the above-described embodiments, an output (e.g. musical notes) produced by the human-computer interface device may be produced by a component of the device, such as, for example, an output device (e.g. a speaker) attached to the device (e.g. disposed in the handle). Additionally or alternatively, the output may be an appropriate output signal to be transmitted to an adjoining host computer (e.g. connected via USB). The host computer may be configured in use to interpret the output signal received from the human-computer interface device and generate an appropriate output in dependence on the signal. For example, if the human-computer interface device is configured to be a recorder the device itself may produce a recorder sound and/or a host computer connected to the device may produce the recorder sound.

In the above-described embodiments of the human-computer interface device, the device is configured to connect to a host computer, for example, by a wireless or wired connection. Accordingly, in such embodiments, the device may be thought of as interfacing in-between a human user of the device and the host computer to which the device is connected. Accordingly, the host computer and/or the device may generate the output (e.g. musical note). However, in some other embodiments, the device may be a standalone device, i.e. the device may not need to be connected to a host computer in order to operate. In such embodiments, the device may still be thought of as a human-computer interface device which interfaces between the human user of the device and a computer (e.g. microcontroller) of the device. Accordingly, the device itself may generate the output (e.g. musical note).

Example applications implementing the array according to an embodiment of the present invention have been described above. It will be appreciated by a person skilled in the art that that by incorporating sensors and/or actuators, the array is able to, among other things, alter its shape, alter its flexibility, produce sounds and/or tactile feedback to enhance human-computer interaction. Having dynamic human-computer interfaces that are capable of changing their physical properties may advantageously provide more immersive and engaging human-computer interaction.

It will be appreciated by a person skilled in the art that numerous variations and/or modifications may be made to the present invention as shown in the embodiments without departing from a spirit or scope of the invention as broadly described. The embodiments are, therefore, to be considered in all respects to be illustrative and not restrictive.

The invention claimed is:

1. A human-computer interface device, comprising:
   an array of elements, wherein each element is pivotally coupled to an adjacent first element by a first pivotal coupling and to an adjacent second element by a second pivotal coupling, the first pivotal coupling being operable to pivot about an axis which is substantially orthogonal to an axis about which the second pivotal coupling is operable to pivot; and
   one or more actuators configured to displace one or more elements of the array.

2. The human-computer interface as claimed in claim 1, wherein at least four elements are arranged to form a grid, each element of the grid being pivotally coupled to each adjacent element in the grid.

3. The human-computer interface as claimed in claim 2, wherein the grid has a square shape.

4. The human-computer interface as claimed in claim 2, wherein the grid has an elongate shape.

5. The human-computer interface as claimed in claim 1, wherein each first pivotal coupling is operable to pivot about the same axis to prevent each second pivotal coupling from pivoting.

6. The human-computer interface as claimed in claim 1, wherein adjacent elements are arranged side-by-side.

7. The human-computer interface as claimed in claim 1, wherein the first pivotal coupling is disposed substantially orthogonal to the second pivotal coupling.

8. The human-computer interface as claimed in claim 1, wherein at least one pivotal coupling is capable of only one degree of freedom.

9. The human-computer interface as claimed in claim 1, wherein at least one pivotal coupling comprises at least one hinge.

10. The human-computer interface as claimed in claim 1 wherein at least one element comprises a substantially planar square shape having pivotal couplings positioned at a side portion thereof.

11. The human-computer interface as claimed in claim 1, wherein at least one element has at least one beveled side portion.

12. The human-computer interface device as claimed in claim 1, the device comprising a controller configured in use to provide an output signal.

13. The human-computer interface device as claimed in claim 12, the device comprising
   at least one sensor in communication with the controller, the at least one sensor being operable to detect the relative displacement between at least two elements of the array and provide a corresponding signal to the controller, wherein the controller is operable to provide the output signal in dependence on the corresponding signal.

14. The human-computer interface device as claimed in claim 12, further comprising at least one button disposed on an element of the array, the at least one button being in communication with the controller, wherein the controller is operable to provide the output signal in dependence on activation of the at least one button.

15. The human-computer interface device as claimed in claim 12, further comprising at least one accelerometer for detecting motion of the human-computer interface device, the at least one accelerometer being in communication with the controller, wherein the controller is operable to provide the output signal in dependence on a signal received from the at least one accelerometer.

16. The human-computer interface device as claimed in claim 12, further comprising an output device in communication with the controller, the output device being configured to receive the output signal and provide an output in dependence thereon.

17. The human-computer interface device as claimed in claim 16, wherein the output comprises a sound and/or tactile feedback.

18. The human-computer interface device as claimed in claim 1, further comprising a host computer interface device for enabling data transfer between the human-computer interface device and the host computer.

* * * * *